United States Patent
Islam et al.

(10) Patent No.: US 9,816,846 B2
(45) Date of Patent: Nov. 14, 2017

(54) APPARATUS AND METHOD FOR DETERMINING A NON-CONDENSABLE GAS PARAMETER

(71) Applicant: Spirax-Sarco Limited, Cheltenham, Gloucestershire (GB)

(72) Inventors: Nashtara Islam, Cheltenham (GB); Peter Usher, Cheltenham (GB); Ben Frisby, Cheltenham (GB); David Oliver, Cheltenham (GB)

(73) Assignee: Spirax-Sarco Limited, Cheltenham (GB)

( * ) Notice: Subject to any disclaimer, the term of this patent is extended or adjusted under 35 U.S.C. 154(b) by 311 days.

(21) Appl. No.: 14/491,478

(22) Filed: Sep. 19, 2014

(65) Prior Publication Data

US 2015/0082910 A1   Mar. 26, 2015

(30) Foreign Application Priority Data

Sep. 20, 2013   (GB) .................................. 1316760.6

(51) Int. Cl.
  G01F 1/66     (2006.01)
  G01F 1/05     (2006.01)
  (Continued)

(52) U.S. Cl.
  CPC .................. G01F 1/66 (2013.01); G01F 1/05 (2013.01); G01F 1/68 (2013.01); G01N 29/032 (2013.01);
  (Continued)

(58) Field of Classification Search
  CPC .... G01F 1/05; G01F 1/66; G01F 1/68; G01N 29/032; G01N 2291/02433; G01N 2291/02818; G01N 2291/02836
  (Continued)

(56) References Cited

U.S. PATENT DOCUMENTS

| 4,739,647 A | 4/1988 | Monticelli, Jr. |
| 4,831,867 A | 5/1989 | Vasseur et al. |
| 5,394,732 A | 3/1995 | Johnson et al. |

FOREIGN PATENT DOCUMENTS

| CN | 203154860 U | 8/2013 |
| DE | 3636716 A1  | 5/1988 |

(Continued)

OTHER PUBLICATIONS

Intellectual Property Office of Great Britain, "Search Report," issued in connection with GB1316760.6, dated Mar. 12, 2014, 1 page.

(Continued)

Primary Examiner — Daniel S Larkin
(74) Attorney, Agent, or Firm — Banner & Witcoff, Ltd.

(57) ABSTRACT

System and methods for determining a non-condensable gas parameter relating to the amount of non-condensable gas within a variable flow rate fluid flow containing both non-condensable gas and condensate are disclosed. An apparatus may include a measurement tube for receiving the fluid flow and arranged such that the fluid flow through the measurement tube comprises alternating sections of non-condensable gas and condensate; a flow sensor for generating a flow rate signal relating to the flow rate of the fluid flow in the measurement tube; a phase sensor for monitoring over time the alternating sections of non-condensable gas and condensate flowing through the measurement tube and arranged generates a phase signal characteristic of the said sections monitored; and a non-condensable gas determining unit configured to determine a non-condensable gas parameter relating to the amount of non-condensable gas in the fluid flow based on the flow rate signal and phase signal.

18 Claims, 4 Drawing Sheets

(51) Int. Cl.
  *G01F 1/68* (2006.01)
  *G01N 29/032* (2006.01)
(52) U.S. Cl.
  CPC .............. *G01N 2291/02433* (2013.01); *G01N 2291/02818* (2013.01); *G01N 2291/02836* (2013.01)
(58) Field of Classification Search
  USPC .............................................. 73/19.01, 19.1
  See application file for complete search history.

(56) References Cited

FOREIGN PATENT DOCUMENTS

| | | |
|---|---|---|
| EP | 1715302 A1 | 10/2006 |
| EP | 2333331 A1 | 6/2011 |
| JP | S56140274 A | 11/1981 |

OTHER PUBLICATIONS

Jun. 1, 2017—(CN) Office Action—App. No. 201410482936.2—10 pages.

APPARATUS AND METHOD FOR DETERMINING A NON-CONDENSABLE GAS PARAMETER

CROSS-REFERENCE TO RELATED APPLICATIONS

The present application claims priority to GB 1316760.6, filed on 20 Sep. 2013, which is hereby incorporated by reference in its entirety for any and all non-limiting purposes.

BACKGROUND

The invention relates to an apparatus and method for determining a non-condensable gas parameter relating to the amount of non-condensable gas within a fluid flow containing both non-condensable gas and condensate.

The presence of non-condensable gas, such as air, within a steam flow can significantly alter the properties of the steam flow. For example, non-condensable gas may affect the heat transfer properties of the steam flow. Further, non-condensable gas may lead to heterogeneous steam properties within the steam flow, such as regions of superheated steam and regions of saturated steam.

In a number of industrial processes, it is desirable to minimize the amount of non-condensable gas within a steam flow. One such example is the sterilization of products and/or equipment in a steam flow, for example in the medical and pharmaceutical industries. If the amount of non-condensable gas within the steam flow is too high, the heat transfer rate between the steam flow and the equipment may be insufficient to properly sterilize the equipment.

It is known to measure the amount of non-condensable gas in a steam flow by condensing a sample of the steam and collecting the resultant non-condensable gas and condensate. European Standard EN 285 defines a safety limit of 3.5 ml of non-condensable gas per 100 ml of condensate, or 3.5%, for sterilization applications.

Non-condensable gas may be introduced into a steam system in a number of ways. For example, non-condensable gas can be introduced by excessive aeration during water treatment, such as water softening. Further, non-condensable gas can be introduced into a steam system upstream of a boiler if the inlet water for the boiler is not pre-heated sufficiently, since non-condensable gas (e.g. air) is more easily absorbed in water at lower temperatures. Insufficient pre-heating may occur in a variable demand steam system when the amount of steam demanded from the boiler is increased, therefore increasing the flow rate of inlet water through the pre-heater to the boiler.

U.S. Pat. No. 4,831,867 discloses a method and apparatus for estimating the proportion of non-condensable gas within a steam flow by extracting a portion of the steam flow and condensing it to provide a fluid flow of substantially constant flow rate containing bubbles of non-condensable gas and drops of liquid condensate. An optical sensor records the cumulative time that non-condensable gas bubbles pass the sensor, and the cumulative time that condensate drops pass the sensor. It is assumed that the ratio of the respective lengths of the gas and condensate passing the sensor are constant, and that the flow rate is substantially constant. Accordingly, the method and apparatus only compares the cumulative times of gas and condensate flowing past the sensor in order to estimate the proportion of non-condensable gas within the steam flow.

However, the estimate of the proportion of non-condensable gas may be inaccurate where the flow rate of the fluid flow is variable, and where the respective steam flow has a varying proportion of non-condensable gas.

Accordingly, it is desirable to provide an improved apparatus and method for measuring the amount of non-condensable gas in a fluid flow.

SUMMARY

According to a first aspect of the invention there is provided an apparatus for determining a non-condensable gas parameter relating to the amount of non-condensable gas within a variable flow rate fluid flow containing both non-condensable gas and condensate, the apparatus comprising: a measurement tube for receiving the fluid flow and arranged such that the fluid flow through the measurement tube comprises alternating sections of non-condensable gas and condensate; a flow sensor for generating a flow rate signal relating to the flow rate of the fluid flow in the measurement tube; a phase sensor for monitoring over time the alternating sections of non-condensable gas and condensate flowing through the measurement tube and arranged to generate a phase signal characteristic of the sections monitored; and a non-condensable gas determining unit configured to determine a non-condensable gas parameter relating to the amount of non-condensable gas in the fluid flow based on the flow rate signal and the phase signal.

The phase signal may be a time-varying profile characteristic of the sections monitored. The phase signal may be characteristic of the time-lengths of the sections monitored. The phase sensor may be arranged to determine the phase of the fluid flow flowing through the measurement tube. The phase sensor may be arranged to determine whether the fluid flow flowing through the measurement tube is condensate or non-condensable gas.

The flow rate signal may be a time-varying flow rate signal. The flow rate signal may relate to the velocity flow rate of the fluid flow.

The non-condensable gas determining unit may be configured to determine a non-condensable gas parameter at least partly by correlating the phase signal with the flow rate signal. Correlating the phase signal with the flow rate signal may comprise mapping the phase signal onto the flow rate signal or vice versa. Correlating the phase signal with the flow rate signal may comprise pairing portions of the phase signal with portions of the flow rate signal. The non-condensable gas determining unit may be configured to determine a non-condensable gas parameter at least partly by determining the time-lengths of sections of non-condensable gas and/or condensate from the phase signal, and correlating them with corresponding parts of the flow rate signal.

The non-condensable gas determining unit may be configured to determine a non-condensable gas parameter at least partly by calculating a gas volume parameter proportional to the volume of the monitored sections of non-condensable gas.

The non-condensable gas determining unit may be configured to determine a non-condensable gas parameter at least partly by calculating a condensate volume parameter proportional to the volume of the monitored sections of condensate. The non-condensable gas determining unit may be configured to determine the non-condensable gas parameter at least partly by calculating a non-condensable gas ratio parameter corresponding to the ratio of the gas volume parameter and the condensate volume parameter, or the ratio of the gas volume parameter and the sum of the gas volume parameter and the condensate volume parameter. The non-condensable gas parameter may be proportional to the non-condensable gas ratio parameter.

The apparatus may further comprise a temperature sensor for generating a temperature signal relating to the temperature of the fluid flow in the measurement tube, and the non-condensable gas determining unit may be configured to determine a non-condensable gas parameter relating to the amount of non-condensable gas in the fluid flow at a baseline temperature based on the temperature signal, the flow signal and the phase signal. The non-condensable gas parameter may be at least partly determined based on a signal or quantity relating to the baseline temperature, which may be the baseline temperature. The baseline temperature may be different from the temperature of the fluid flow in the measurement tube. The amount of non-condensable gas in the fluid flow at the baseline temperature may be different from the amount of non-condensable gas in the fluid flow at prevailing temperature conditions (i.e. the actual temperature of the fluid flow in the measurement tube), for example, owing to temperature effects on the volume of the gas described by the ideal gas law.

The non-condensable gas determining unit may be configured to determine the non-condensable gas parameter relating to the amount of non-condensable gas in the fluid flow at the baseline temperature at least partly by calculating a non-condensable gas volume parameter proportional to the volume of the monitored sections of non-condensable gas and by scaling the non-condensable gas volume parameter based on the temperature of the fluid flow in the measurement tube and the baseline temperature. The non-condensable gas determining unit may be configured to scale the non-condensable gas volume parameter based on a ratio of the baseline temperature and the temperature of the fluid flow in the measurement tube.

The apparatus may be configured so that the temperature of the fluid flow in the measurement tube is less than the baseline temperature. The apparatus may be configured so that the temperature of the fluid flow in the measurement tube is approximately 40° C. The baseline temperature may be 80° C.

The apparatus may further comprise a pressure sensor for generating a pressure signal relating to the pressure of the fluid flow in the measurement tube, and the non-condensable gas determining unit may be configured to determine a non-condensable gas parameter relating to the amount of non-condensable gas in the fluid flow at a baseline pressure based on the pressure signal, the flow signal and the phase signal. The non-condensable gas parameter may be at least partly determined based on a signal or quantity relating to the baseline pressure, which may be the baseline pressure. The baseline pressure may be different from the pressure of the fluid flow in the measurement tube.

The non-condensable gas determining unit may be configured to determine the non-condensable gas parameter relating to the amount of non-condensable gas in the fluid flow at the baseline pressure at least partly by calculating a non-condensable gas volume parameter proportional to the volume of the monitored sections of non-condensable gas and by scaling the non-condensable gas volume parameter based on the pressure of the fluid flow in the measurement tube and the baseline pressure. The non-condensable gas determining unit may be configured to scale the non-condensable gas volume parameter based on a ratio of the baseline pressure and the pressure of the fluid flow in the measurement tube.

The apparatus may be configured so that the pressure of the fluid flow in the measurement tube is higher or lower than the baseline pressure. The baseline pressure may be at or near atmospheric pressure. The baseline pressure may be 1 atmosphere or 1 bar.

The non-condensable gas parameter may represent the relative amount of non-condensable gas with respect to the amount of condensate or the amount of fluid flow.

The non-condensable gas determining unit may determine the non-condensable gas parameter over a sampling period in which a plurality of alternating sections of non-condensable gas and condensate flow through the measurement tube.

The phase sensor may comprise an optical sensor responsive to the refractive index of the fluid flow in the measurement tube. The phase sensor may comprise an ultrasonic sensor responsive to the density of the fluid flow in the measurement tube.

The flow sensor may comprise an ultrasonic flow sensor.

The apparatus may further comprise a gas vent for venting non-condensable gas from the fluid flow. The gas vent may be disposed downstream of the phase sensor and upstream of the flow sensor.

According to a second aspect of the invention there is provided a steam installation comprising: an apparatus in accordance with the first aspect of the invention; and a condenser arranged to receive a steam flow and arranged to condense the steam flow to provide a fluid flow containing both non-condensable gas and condensate.

The installation may further comprise a steam extractor for extracting the steam flow from a main steam flow. The steam extractor may be arranged such that the flow rate of the steam flow extracted from the main steam flow is dependent on the pressure of the main steam flow.

According to a third aspect of the invention there is provided a method of determining a non-condensable gas parameter relating to the amount of non-condensable gas within a variable flow rate fluid flow containing both non-condensable gas and condensate, the method comprising: receiving the fluid flow in a measurement tube thereby causing the fluid flow through the measurement tube to comprise alternating sections of non-condensable gas and condensate; generating a flow rate signal relating to the flow rate of the fluid flow in the measurement tube; monitoring the alternating sections of non-condensable gas and condensate flowing through the measurement tube over time; generating a phase signal characteristic of the sections monitored; and determining a non-condensable gas parameter relating to the amount of non-condensable gas in the fluid flow based on the flow rate signal and the phase signal.

The phase signal may be a time-varying profile characteristic of the sections monitored. The phase signal may be characteristic of the time-lengths of the sections monitored. Monitoring the sections may comprise determining the phase of the fluid flow flowing through the measurement tube. Monitoring the sections may comprise determining whether the fluid flow flowing through the measurement tube is condensate or non-condensable gas.

The flow rate signal may be a time-varying flow rate signal. The flow rate signal may relate to the velocity flow rate of the fluid flow.

Determining the non-condensable gas parameter may comprise correlating the phase signal with the flow rate signal. Correlating the phase signal with the flow rate signal may comprise mapping the phase signal onto the flow rate signal or vice versa. Determining the non-condensable gas parameter may comprise determining the time-lengths of sections of non-condensable gas and/or condensate from the phase signal, and correlating them with corresponding parts of the flow rate signal.

Determining the non-condensable gas parameter may comprise calculating a non-condensable gas volume parameter proportional to the volume of the monitored sections of non-condensable gas Determining the non-condensable gas parameter may comprise calculating a condensate volume parameter proportional to the volume of the monitored sections of condensate. Determining the non-condensable gas parameter may comprise calculating a non-condensable gas ratio parameter by determining the ratio of the gas volume parameter and the condensate volume parameter, or the ratio of the gas volume parameter and the sum of the gas volume parameter and the condensate volume parameter. The non-condensable gas parameter may be proportional to the non-condensable gas ratio parameter.

The method may further comprise generating a temperature signal relating to the temperature of the fluid flow in the measurement tube, and the non-condensable gas parameter may be determined so as to relate to the amount of non-condensable gas in the fluid flow at a baseline temperature based on the temperature signal, the flow signal and the phase signal. The determination may also be based on a signal or quantity relating to the baseline temperature, which may be the baseline temperature. The baseline temperature may be different from the temperature of the fluid flow in the measurement tube.

Determining the non-condensable gas parameter may comprise calculating a non-condensable gas volume parameter proportional to the volume of the monitored sections of non-condensable gas and scaling the non-condensable gas volume parameter based on the temperature of the fluid flow in the measurement tube and the baseline temperature. Scaling the non-condensable gas volume parameter may be based on a ratio of the baseline temperature and the temperature of the fluid flow in the measurement tube.

The temperature of the fluid flow in the measurement tube may be less than the baseline temperature. The temperature of the fluid flow in the measurement tube may be approximately 40° C. The baseline temperature may be 80° C.

The method may further comprise generating a pressure signal relating to the pressure of the fluid flow in the measurement tube, and the non-condensable gas parameter may relate to the amount of non-condensable gas in the fluid flow at a baseline pressure different from the pressure of the fluid flow in the measurement tube based on the pressure signal, the flow signal and the phase signal. The determination may also be based on a signal or quantity relating to the baseline pressure, which may be the baseline pressure. The baseline pressure may be different from the pressure of the fluid flow in the measurement tube.

Determining the non-condensable gas parameter may comprise calculating a non-condensable gas volume parameter proportional to the volume of the monitored sections of non-condensable gas and scaling the non-condensable gas volume parameter based on the pressure of the fluid flow in the measurement tube and the baseline pressure. Scaling the non-condensable gas volume parameter may be based on a ratio of the baseline pressure and the pressure of the fluid flow in the measurement tube.

The pressure of the fluid flow in the measurement tube may be higher or lower than the baseline pressure. The baseline pressure may be at or near atmospheric pressure. The baseline pressure may be 1 atmosphere or 1 bar.

The non-condensable gas parameter may represent the relative amount of non-condensable gas with respect to the amount of condensate or the amount of fluid flow.

Determining the non-condensable gas parameter may be carried out over a sampling period in which a plurality of alternating sections of non-condensable gas and condensate flow through the measurement tube.

The method may further comprise venting the non-condensable gas from the fluid flow at a position downstream of a phase sensor which monitors the sections and generates the phase signal characteristic of the sections, and upstream of a flow sensor which generates the flow rate signal.

According to a fourth aspect of the invention there is provided a method of operating a steam installation comprising a method of determining a non-condensable gas parameter in accordance with the third aspect of the invention, and further comprising: receiving a steam flow; and condensing the steam flow to provide a fluid flow containing both non-condensable gas and condensate.

The method may further comprise extracting the steam flow from a main steam flow. The flow rate of the steam flow extracted from the main steam flow may be dependent on the pressure of the main steam flow.

According to a fifth aspect of the invention there is provided an apparatus for determining a non-condensable gas parameter relating the amount of non-condensable gas within a fluid flow containing both non-condensable gas and condensate, the apparatus comprising: a measurement tube for receiving the fluid flow and arranged such that the fluid flow through the measurement tube comprises alternating sections of non-condensable gas and condensate; a phase sensor for monitoring over time the alternating sections of non-condensable gas and condensate flowing through the measurement tube and arranged to generate a phase signal characteristic of the said sections monitored; a temperature sensor for generating a temperature signal relating to the temperature of the fluid flow in the measurement tube; and a non-condensable gas determining unit configured to determine a non-condensable gas parameter relating to the amount by of non-condensable gas in the fluid flow at a baseline temperature based on the phase signal and the temperature signal. The baseline temperature may be different from the temperature of the fluid flow in the measurement tube.

According to a sixth aspect of the invention there is provided an apparatus for determining a non-condensable gas parameter relating the amount of non-condensable gas within a fluid flow containing both non-condensable gas and condensate, the apparatus comprising: a measurement tube for receiving the fluid flow and arranged such that the fluid flow through the measurement tube comprises alternating sections of non-condensable gas and condensate; a phase sensor for monitoring over time the alternating sections of non-condensable gas and condensate flowing through the measurement tube and arranged to generate a phase signal characteristic of the sections monitored; a pressure sensor for generating a pressure signal relating to the pressure of the fluid flow in the measurement tube; and a non-condensable gas determining unit configured to determine a non-condensable gas parameter relating to the amount by of non-condensable gas in the fluid flow at a baseline pressure based on the phase signal and the pressure signal. The baseline pressure may be different from the pressure of the fluid flow in the measurement tube.

The non-condensable gas determining unit of apparatus in accordance with the fifth and/or sixth aspects of the invention may be configured to determine the non-condensable gas parameter at least partly by calculating a non-condensable gas volume parameter proportional to the volume of the monitored sections of non-condensable gas. The non-condensable gas volume parameter may be calculated based on the time-lengths of sections of non-condensable gas without monitoring a flow rate, for example, for fluid flows of substantially constant flow rate.

Apparatus in accordance with the fifth and sixth aspects of the invention may comprise a flow regulator configured so that the flow rate of fluid flow received at the measuring tube is substantially constant.

Apparatus in accordance with the fifth and sixth aspects of the invention may comprise any of the features and limitations specified in respect of the other aspects of the invention, except such features as are mutually exclusive.

According to a seventh aspect of the invention there is provided a method of determining a non-condensable gas parameter relating to the amount of non-condensable gas within a fluid flow containing both non-condensable gas and condensate, the method comprising: receiving the fluid flow in a measurement tube thereby causing the fluid flow through the measurement tube to comprise alternating sections of non-condensable gas and condensate; monitoring the alternating sections of non-condensable gas and condensate flowing through the measurement tube over time; generating a phase signal characteristic of the sections monitored; generating a temperature signal relating to the temperature of the fluid flow in the measurement tube; and determining a non-condensable gas parameter relating to the amount of non-condensable gas in the fluid flow at a baseline based on the phase signal and the temperature signal. The baseline temperature may be different from the temperature of the fluid flow in the measurement tube.

According to an eighth aspect of the invention there is provided a method of determining a non-condensable gas parameter relating to the amount of non-condensable gas within a fluid flow containing both non-condensable gas and condensate, the method comprising: receiving the fluid flow in a measurement tube thereby causing the fluid flow through the measurement tube to comprise alternating sections of non-condensable gas and condensate; monitoring the alternating sections of non-condensable gas and condensate flowing through the measurement tube over time; generating a phase signal characteristic of the sections monitored; generating a pressure signal relating to the pressure of the fluid flow in the measurement tube; and determining a non-condensable gas parameter relating to the amount of non-condensable gas in the fluid flow at a baseline pressure based on the phase signal and the pressure signal. The baseline temperature may be different from the temperature of the fluid flow in the measurement tube.

The step of determining the non-condensable gas parameter in methods in accordance with the seventh and/or eighth aspects may comprise calculating a non-condensable gas volume parameter proportional to the volume of the monitored sections of non-condensable gas. The non-condensable gas volume parameter may be calculated based on the time-lengths of sections of non-condensable gas without monitoring a flow rate, for example, for fluid flows of substantially constant flow rate.

A method in accordance with the seventh and/or eighth aspects of the invention may further comprise regulating the fluid flow so that the flow rate of fluid flow received at the measuring tube is substantially constant.

A method in accordance with the seventh and/or eighth aspects of the invention may comprise any of the features and limitations specified in respect of the other aspects of the invention, except such features as are mutually exclusive.

The invention may comprise any combination of the features and/or limitations referred to herein, except combinations of such features as are mutually exclusive.

BRIEF DESCRIPTION OF DRAWINGS

Embodiments of the invention will now be described, by way of example, with reference to the accompanying drawings, in which.

DETAILED DESCRIPTION

Figure 1:
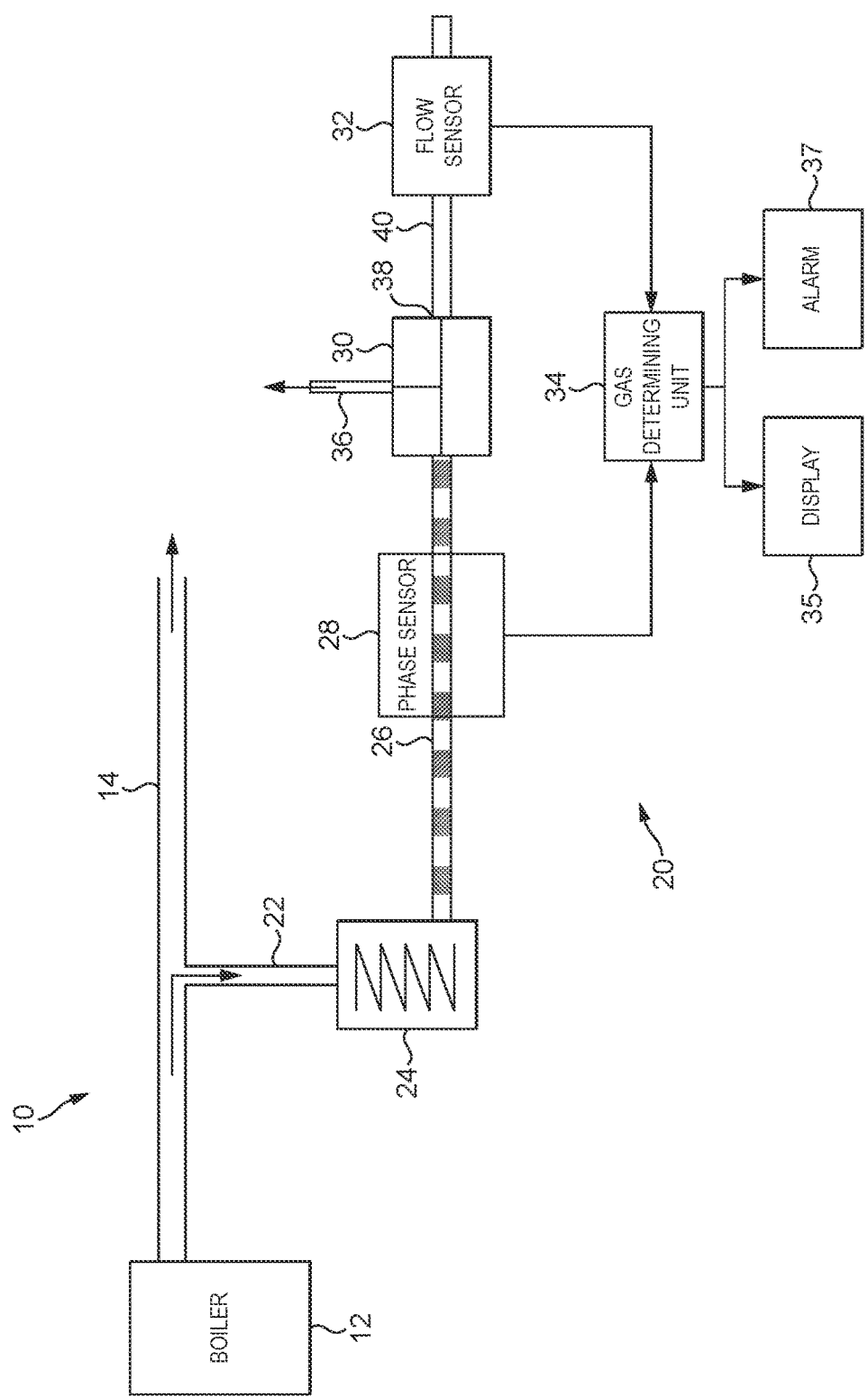
FIG. 1 schematically shows an apparatus according to an embodiment of the invention.

FIG. 1 shows a part of a steam system 10 and a measurement apparatus 20 for measuring the amount of non-condensable gas in a variable flow rate fluid flow derived from the steam system 10.

The steam system 10 comprises a boiler 12 and a main steam flow line 14 for a main steam flow. The measurement apparatus 20 comprises a branch line 22 connected to the main steam flow line 14 and which feeds a condenser 24 the steam extracted from the main steam flow line 14. The condenser 24 provides a fluid flow containing both non-condensable gas and condensate.

The measurement apparatus further comprises a measurement tube 26, a phase sensor 28, a gas vent 30, flow sensor 32, a non-condensable gas determining unit 34 and a display 35 and alarm 37.

The measurement tube 26 is arranged to receive fluid flow from the condenser 24 and is of sufficiently small diameter that the fluid flow flowing therethrough comprises alternating sections of non-condensable gas (i.e. bubbles) and condensate (i.e. liquid drops). The diameter of the measurement tube 26 may be between 0.5 mm and 4 mm, or between 1 mm and 2 mm, for example.

The measurement tube 26 extends through the phase sensor 28 which in this embodiment is an ultrasonic bubble sensor. Therefore, the section of the measurement tube extending through the phase sensor 28 is formed from a material suitable for the transmission of ultrasonic waves. In this embodiment the section of the measurement tube extending through the phase sensor is a plastics material with high temperature resistance, such as PTFE. The section of the measurement tube extending through the phase sensor 28 also has a degree of flexibility to aid installation.

The ultrasonic bubble sensor 28 is capable of detecting whether the fluid flow in the measurement tube 26 at the location at which it monitors is non-condensable gas or condensate. The ultrasonic bubble sensor comprises an ultrasonic pulse emitter on one side of the tube, and a receiver at the opposite side of the tube. In operation, the pulse emitter emits an ultrasonic pulse which passes through the measurement tube and the fluid flow and is received by the receiver. Depending on the attenuation of the signal received by the receiver, it can be determined whether the pulse has passed through a section of non-condensable gas or a section of condensate.

The gas vent 30 is coupled to the end of the measurement tube 26 downstream of the phase sensor 28. The vent 30 receives the fluid flow from the measurement tube 26 and removes the non-condensable gas therefrom. The gas vent 30 is an automatic component having a gas release valve that opens when gas flows into the vent. The gas vent 30 has a gas exhaust line 36 for exhausting non-condensable gas and a liquid exit port 38 for the condensate. The gas vent may be any suitable automatic gas vent, such as a Spirax-Sarco AE30 Air Eliminator.

The flow sensor 32 is coupled to a flow line 40 extending from the liquid exit port 38 of the gas vent 30. In this embodiment, the flow sensor is an ultrasonic flow sensor and the flow line 40 extends through the flow sensor 32. The ultrasonic flow sensor 32 is arranged to monitor the flow rate of the fluid flow in the flow line 40 by transmitting ultrasonic pulses through the flow line 40 both upstream and downstream. The flow sensor 32 comprises upstream and downstream receivers which receive the transmitted ultrasonic pulses. The sensor 32 determines the time of flight of the pulses through the fluid flow in both the upstream and downstream directions and the difference between the upstream and downstream time of flight relates to the velocity flow rate of the fluid flow. The flow sensor 32 is arranged to generate a time-varying flow rate signal that relates to the velocity flow rate of the fluid flow.

The non-condensable gas determining unit 34 is connected to the phase sensor 28 and the flow sensor 32 and receives the phase signal and flow rate signal from the respective sensors. In this embodiment the phase signal and flow rate signal are transmitted to the non-condensable gas determining unit 34 via a wired link, but in other embodiments the phase signal and/or flow rate signal may be transmitted via a wireless link. The non-condensable gas determining unit 34 is configured to determine a non-condensable gas parameter relating to the amount of non-condensable gas in the fluid flow using both the phase signal and the flow rate signal. In this embodiment the non-condensable gas determining unit 34 is configured to correlate the phase signal with the flow rate signal to determine a non-condensable gas parameter that relates to the percentage of non-condensable gas in the fluid flow (by volume).

In this embodiment the non-condensable gas determining unit is a dedicated unit having inputs for receiving the phase signal and the flow rate signal, and an output for the display 35 and alarm 37. However, in other embodiments, the non-condensable gas determining unit 34 may incorporate the display and alarm, or may be a computer provided with appropriate software.

The measurement apparatus 20 further comprises a display 35 and alarm 37. The display 35 is configured to be refreshed whenever the non-condensable gas parameter is updated. The alarm 37 is configured to be activated when the non-condensable gas parameter indicates an amount of non-condensable gas higher than a threshold.

A method for measuring non-condensable gas in a variable flow rate fluid will now be described with reference to the measurement apparatus 20 of FIG. 1.

In use, the boiler 12 boils water received from a pre-heater (not shown) to produce the main steam flow flowing in the main steam line 14. The main steam flow contains non-condensable gas, such as air, and steam. A portion of the main steam flow flows down the branch line 22 to the condenser 24, where it is condensed to produce a fluid flow containing non-condensable gas and condensate.

The fluid flow is received in the measurement tube 26 and forms alternating sections of non-condensable gas bubbles and condensate drops owing to the small diameter of the measurement tube 26. The alternating sections of non-condensable gas and condensate are separated by menisci, and flow through the measurement tube 26 end-to-end at a variable velocity flow rate. The sections of non-condensable gas, or bubbles, occupy the full diameter of the measurement tube 26 and are of varying lengths.

The fluid flow flows in the measurement tube 26 past the ultrasonic bubble sensor 28. The ultrasonic bubble sensor 28 emits and receives an ultrasonic pulse 100,000 times a second. The bubble sensor determines the phase of the fluid flow passing the sensor according to the attenuation of each pulse and generates a corresponding phase signal indicating the phase of the fluid flow for each ultrasonic pulse. The phase signal provides a profile of the phase of the fluid flow over time, which is transmitted to the non-condensable gas determining unit 34 by the wired link.

Downstream of the ultrasonic bubble sensor, the fluid flow enters the gas vent 30 and the non-condensable gas is removed from the fluid flow via a gas exhaust line 36. In this embodiment the gas is vented to atmosphere, but in other embodiments the gas may be collected and conveyed to a heat recovery unit. The fluid flow, now substantially comprising only condensate, exits the gas vent 30 by the liquid exit port 38 to enter the flow line 40.

As the fluid flow flows in the line 40 past the ultrasonic flow sensor 32, the flow sensor 32 generates a flow rate signal relating to the velocity flow rate of the fluid flow. This signal is transmitted to the non-condensable gas determining unit 34 by the wired link. In this embodiment, the flow sensor is calibrated to determine the velocity flow rate of the fluid flow each second in units of meters per second and generate a corresponding flow rate signal. However, it will be appreciated that it is not strictly necessary to determine the actual velocity flow rate of the fluid flow, but only a signal that relates to, or is proportional to, the velocity flow rate.

The non-condensable gas determining unit 34 receives the phase signal from the phase sensor 28 and the flow rate signal from the flow sensor 32. In this embodiment, the flow rate signal corresponds to the velocity flow rate of the fluid flow over time and is updated each second. Since the flow sensor 32 is positioned downstream of the gas vent 30, the flow rate signal is based on the condensate fraction of the fluid flow. However, the flow rate of the condensate fraction of the fluid flow is representative of the flow rate of the combined fluid flow comprising both condensate and non-condensable gas, owing to the typically low proportion of non-condensable gas within the fluid flow.

The phase signal indicates the phase of the fluid flow past the phase sensor 28 100,000 times a second, i.e. for each ultrasonic pulse at intervals of ten microseconds. Since the length of any particular section of non-condensable gas or condensate is significantly longer than ten microseconds, the non-condensable gas determining unit 34 is able to accurately determine the time-length of each section of non-condensable gas or condensate.

For each section of non-condensable gas or condensate the non-condensable gas determining unit 34 correlates the time-length with a corresponding portion of the flow rate signal. As the flow rate signal is updated once per second, the non-condensable gas determining unit 34 interpolates the velocity flow rate for the portion of the flow rate signal corresponding to the respective section of non-condensable gas or condensate.

The non-condensable gas determining unit 34 determines the volume of the respective section using the time-length of the section and the correlated velocity flow rate. The non-condensable gas determining unit 34 determines the cumulative volume of sections of non-condensable gas and the cumulative volume of sections of condensate over a sampling period of one minute.

In this embodiment, the non-condensable gas determining unit 34 determines a non-condensable gas parameter corresponding to the proportional volume of non-condensable gas with respect to the volume of condensate during each sampling period. For example, if the non-condensable gas determining unit 34 determines a volume of condensate of 100 ml and a volume of non-condensable gas of 3 ml during the sampling period, it will determine a non-condensable gas parameter of 3%.

The non-condensable gas parameter is displayed on the display 35, which is refreshed at the end of each sampling period.

In this embodiment the alarm is configured to be activated if the non-condensable gas parameter exceeds 3.5%, which corresponds to a safety limit for sterilisation applications set in EN 285. In this embodiment, the alarm 37 is an audible alarm but other types of alarms may be provided, such as a visual alarm or a remote alarm.

It will be appreciated that it is not required for the non-condensable gas determining unit 34 to determine the actual volume of non-condensable gas, but only to determine a non-condensable gas parameter that relates to or is proportional to the volume of non-condensable gas. For example, the relative amount of non-condensable gas with respect to the amount of condensate in a fluid flow may be determined without knowing the actual volumes of non-condensable gas and condensate, but by determining parameters which are proportional to the respective volumes. It is therefore only necessary to determine the time-lengths, or the relative time-lengths, of the respective sections of non-condensable gas and condensate, and to correlate these with an associated portion of the flow rate signal.

Similarly, it is not necessary for the actual velocity flow rate to be derived from the flow rate signal in order to calculate the relative amount of non-condensable gas. It is sufficient that the flow rate signal relates to or is proportional to the velocity flow rate, such that the relative volumes of non-condensable gas and condensate can be determined.

In embodiments of the invention where the actual velocity flow rate is derived from the flow rate signal, the non-condensable gas determining unit 34 is able to determine the actual volume of non-condensable gas by multiplying the velocity flow rate with the time-length of non-condensable gas and the diameter of the measurement tube. It will be appreciated that the non-condensable gas determining unit 34 is capable of re-calculating the velocity flow rate in the measurement tube based on the velocity flow rate at the flow sensor where the diameter of the measurement tube differs from the diameter of the flow line.

EXAMPLE

The invention will now be illustrated using an exemplary simplified fluid flow.

In this example, the non-condensable gas determining unit 34 determines the non-condensable gas parameter over a ten second sampling period. For the first five seconds of the sampling period, the flow rate of the fluid flow is two meters per second, and the time-lengths of the alternating sections of condensate and non-condensable gas are one second and 0.02 seconds respectively. After five seconds, the flow rate increases to five meters per second, and the time-lengths of the alternating sections of condensate and non-condensable gas are one second and 0.04 seconds respectively (with only 0.7 seconds of the final section of condensate being monitored).

Accordingly, over the sampling period of 10 seconds, there is an increased flow of non-condensable gas in the last five seconds, owing to the increased time-lengths of the sections of non-condensable gas and the increased flow rate of the fluid flow.

Figure 2:
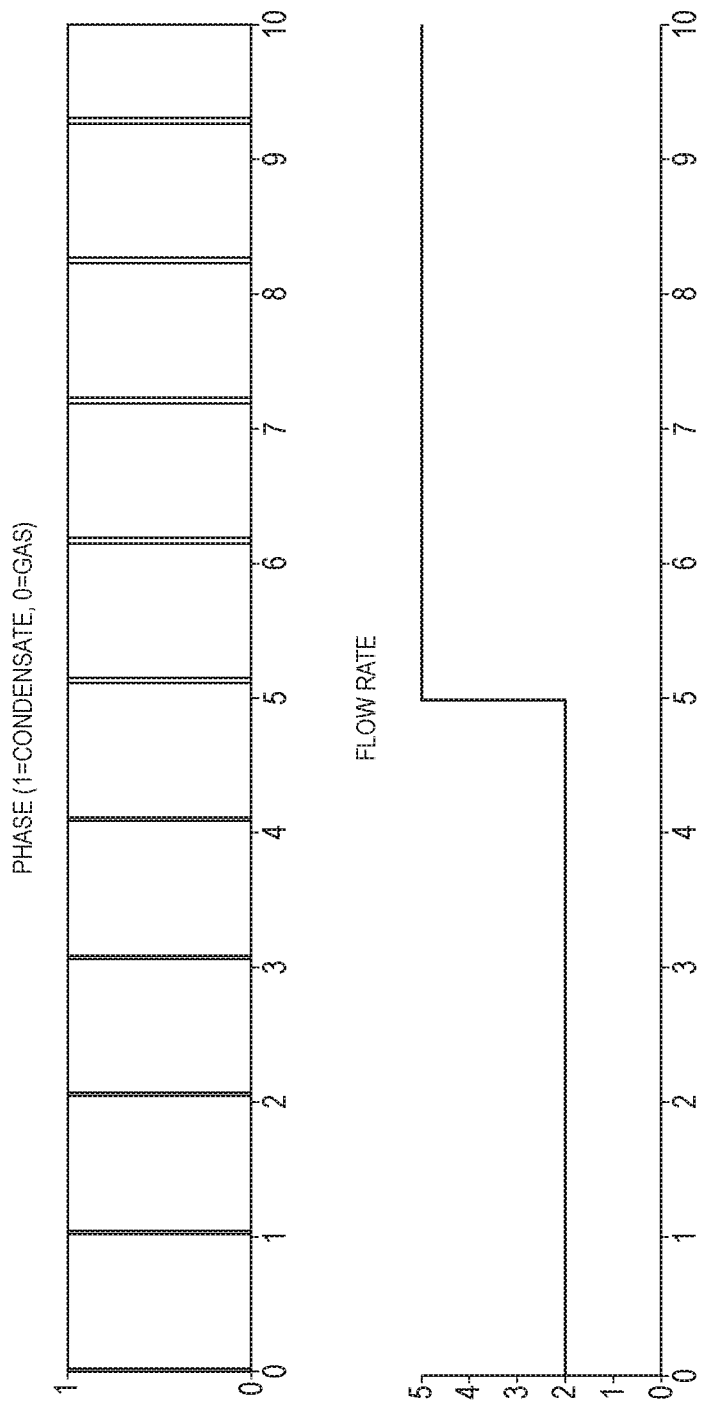
FIG. 2 schematically shows one example of a phase signal and a flow rate signal.

The corresponding phase signal and flow rate signal over the sampling period are shown in FIG. 2.

Estimating the relative proportion of non-condensable gas with respect to the condensate in the fluid flow based on the time-lengths of the respective sections alone provides an estimate of 3% non-condensable gas.

However, measuring the relative proportion of non-condensable gas with respect to condensate in the fluid flow based on the respective volumes of non-condensable gas and condensate provides a measurement of 3.5%.

The measurement based on the respective volumes of non-condensable gas and condensate is more accurate since it takes into account the increased volume flow rate of the fluid flow in the last five seconds, during which the time-lengths of the sections of non-condensable gas increased relative to the sections of condensate.

Figure 3:
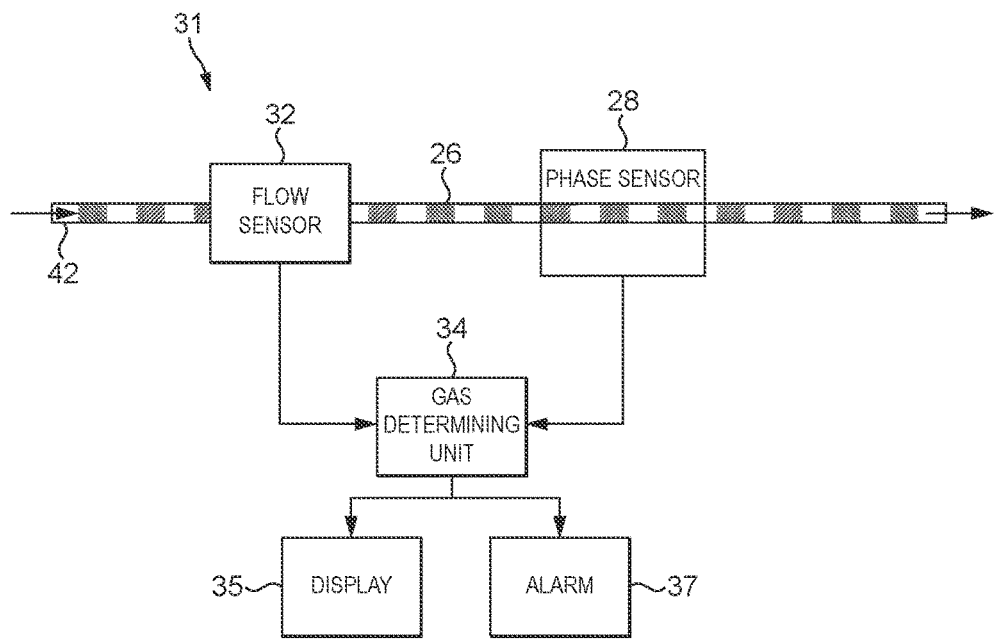
FIG. 3 schematically shows an apparatus according to a second embodiment of the invention.

FIG. 3 shows a second embodiment of a measurement apparatus 31 according to the invention, comprising a measurement tube 26, flow sensor 32, phase sensor 28 and non-condensable gas determining unit 34.

The second embodiment of the measurement apparatus 31 differs from the first embodiment in that the measurement apparatus 31 does not comprise means for extracting a steam flow from a main steam flow line, and does not comprise a condenser. The measurement apparatus is arranged to receive a fluid flow at its inlet 42.

Further, the second embodiment of the measurement apparatus 30 differs from the first embodiment in that the flow sensor 32 is provided upstream of the phase sensor 28, and in that there is no gas vent.

Accordingly, in use, the flow sensor 32 generates the flow rate signal based on both the non-condensable gas fraction and condensate fraction of the fluid flow. In contrast, the flow sensor 32 of the first embodiment generates the flow rate signal based on the condensate fraction of the fluid flow. In other embodiments a Pelton wheel type flow sensor may determine a parameter relating to the flow rate and generate a corresponding signal at regular intervals.

In the second embodiment, the flow sensor 32 is a Pelton wheel type flow sensor. In use, the flow sensor 32 generates a signal at a frequency relating to the flow rate of the fluid flow. The non-condensable gas determining unit 34 interprets the frequency to determine a parameter relating to the flow rate of the fluid flow.

In the second embodiment, the phase sensor is an optical sensor of the type described in U.S. Pat. No. 4,831,867 (columns 4 and 5) and the portion of the measurement tube 26 coupled to or passing through the optical sensor is transparent or semi-transparent accordingly. This portion of the measurement tube 26 is made of a material having a refractive index relatively closely matched to the refractive index of the condensate, such as glass or a plastics material. For example, the condensate may have a refractive index of 1.33, and a glass measurement tube may have a refractive index of 1.5.

The optical sensor has a light beam transmitter which periodically emits a light beam, and a receiver. In use, when a section of condensate passes the optical sensor, the light beam is deflected through a relatively small angle such that the receiver detects the light beam. However, when a section of non-condensable gas passes the optical sensor, the light beam is deflected through a larger angle such that the receiver does not detect the light beam. Accordingly, the optical sensor is able to detect the presence of condensate or non-condensable gas in the measurement tube. As with the ultrasonic bubble sensor of the first embodiment, the optical sensor emits light at a high frequency, such as 100,000 times a second.

As with the first embodiment of the invention, the non-condensable gas determining unit 34 determines a non-condensable gas parameter relating to the amount of non-condensable gas in the fluid flow based on the flow rate signal generated by the flow sensor 32 and the phase signal generated by the phase sensor 28.

In yet further embodiments, other types of flow meters or flow sensors may be used, such as a positive displacement flow meter, or a gear flow meter.

Figure 4:
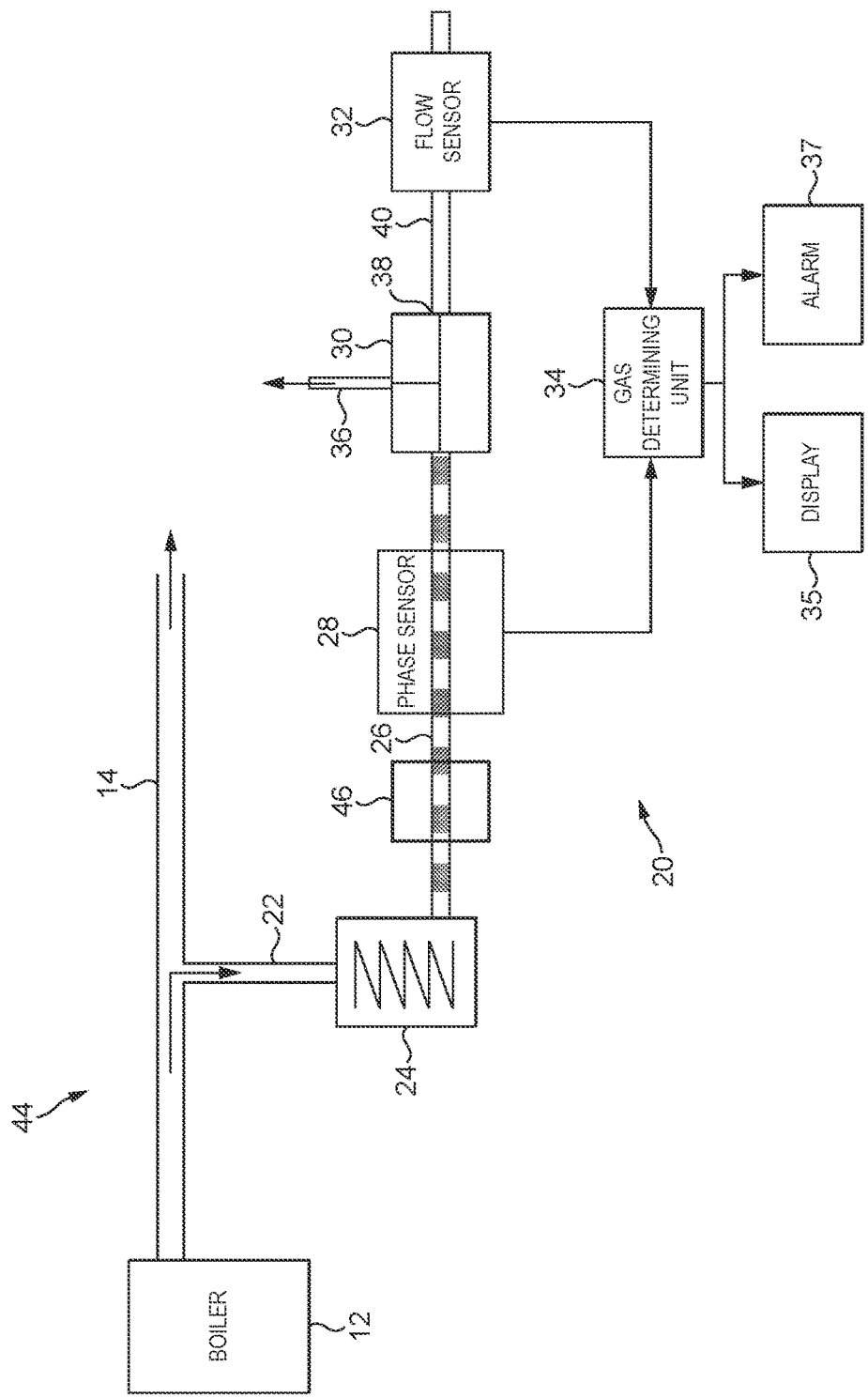
FIG. 4 schematically shows an apparatus according to a third embodiment of the invention.

FIG. 4 shows a third embodiment of a measurement apparatus 44 according to the invention. The third embodiment of the measurement apparatus 44 differs from the first embodiment in that it additionally comprises a temperature sensor 46 disposed between the condenser 24 and the phase sensor 28 and configured to generate a signal relating to the temperature of the fluid flow in the measurement tube 26.

In this embodiment, the non-condensable gas determining unit 34 of the measurement apparatus 44 is configured to determine a non-condensable gas parameter corresponding to an adjusted proportional volume of non-condensable gas with respect to the volume of condensate during each sampling period. The adjusted proportional volume relates to the volume of non-condensable gas at a pre-determined temperature.

For example, the safety limit for sterilization applications that is set in EN285 corresponds to a volumetric proportion of non-condensable gas of 3.5% at 80° C. (and at atmospheric pressure). Owing to the compressibility of gas, the volumetric proportion of non-condensable gas depends on the temperature and pressure of the fluid flow. Accordingly, the non-condensable gas determining unit 34 is configured to adjust the volumetric proportion calculated based on the phase signal and flow rate signal taking into account the temperature difference between the fluid flow in the measurement tube 26 and the pre-determined temperature, such as 80° C. This adjustment is done based on the ideal gas law, as illustrated in Equations 1 to 3 below, in which P is pressure, V is volume, T is temperature, n is the amount of gas (measured in moles) and R is the ideal gas constant.

$$PV = nRT \quad \text{Equation 1}$$

$$\frac{P_1 V_1}{T_1} = \frac{P_2 V_2}{T_2} \quad \text{Equation 2}$$

$$V_2 = \frac{P_1 V_1 T_2}{T_1 P_2} \quad \text{Equation 3}$$

It can therefore be seen that, assuming constant pressure, the volume of a fixed quantity of gas (i.e. a fixed mass) at a first temperature $T_1$ can be scaled by the ratio of $T_2$ to $T_1$ in order to calculate the volume of the same quantity of gas at a second temperature $T_2$. The non-condensable gas determining unit 34 is configured to adjust the volume proportion of gas determined at a temperature $T_1$, such as 40° C., to determine the equivalent volume proportion of non-condensable gas at a pre-determined temperature $T_2$, such as 80° C. The temperature $T_1$ of the fluid flow in the measurement tube 26 is determined based on the temperature signal from the temperature sensor 46.

In use, the measurement apparatus 44 operates as described above with respect to the first embodiment of the invention. In addition, the temperature sensor 46 generates a signal relating to the temperature $T_1$ of the fluid flow in the measurement tube 26. The non-condensable gas determines an adjusted non-condensable gas parameter relating to the volume proportion of non-condensable gas that would be present in the fluid flow if the fluid flow were at a different baseline temperature $T_2$.

In other embodiments, the measurement apparatus 44 may include a pressure sensor for monitoring the pressure $P_1$ of the fluid flow in the measurement tube 26, which may be incorporated into the adjusted volume calculation as shown above. For example, the pressure $P_1$ in the measurement tube may be 1.2 bar, whereas the baseline pressure $P_2$ for the purposes of the adjusted volume proportion calculation may be 1 bar. The pressure sensor may be provided in addition to or in place of the temperature sensor 46.

Determining the non-condensable gas parameter to reflect the amount of non-condensable gas at pressure and/or temperature conditions other than those within the measurement tube means that the non-condensable gas parameter can be determined to reflect pre-determined operating conditions, such as industry standard test conditions, whilst allowing the apparatus to operate at conditions other than the pre-determined conditions.

For example, the pre-determined conditions may correspond to atmospheric pressure and 80° C. temperature, as specified in British Standard EN 285, in order to assess whether the amount of non-condensable gas exceeds a limit proportion specified therein of 3.5% by volume at these conditions. However, the apparatus could be operated at different pressure and/or temperature conditions. For example, the apparatus may be operated at a lower temperature of approximately 40° C. Operating the apparatus at a lower temperature may be beneficial because a lower operating temperature generally means that less expensive and/or simpler equipment may be used, as opposed to specialist equipment for operation at higher temperatures.

The measurement apparatus and method enable the amount of non-condensable gas in a fluid flow containing non-condensable gas and condensate to be more accurately determined, in order to evaluate the suitability of an associated steam flow for an application. In contrast to estimating the amount of non-condensable gas based on the relative time-lengths of sections of non-condensable gas and condensate alone, the measurement apparatus and method determine the amount of non-condensable gas based on a phase signal characteristic of the alternating sections of non-condensable gas and condensate, and a flow rate signal relating to the flow rate of the fluid flow. Accordingly, the measurement apparatus and method allow the amount of non-condensable gas to be determined by correlating the phase signal and the flow rate signal, such that the non-condensable gas parameter relates to the actual volume of non-condensable gas in the fluid flow.

In particular, the measurement apparatus and method allow the amount of non-condensable gas in a fluid flow to be more accurately determined in a variable flow rate fluid flow. For example, the measurement apparatus and method are particularly applicable in applications where the fluid flow rate depends on the pressure or flow rate of an associated steam flow.

Although embodiments of the invention have been described in which the time-length of each section of non-condensable gas or condensate is determined by the non-condensable gas determining unit 34, it will be appreciated that in other embodiments the time-lengths may be determined by the phase sensor and the phase signal may directly relate to the respective time-lengths. Further, the phase signal may relate to the times at which the phase of the fluid flow changes from non-condensable gas to condensate or vice versa. Further, the phase sensor may determine the time-fraction of each phase over a phase sampling period and the phase signal may relate to the time-fraction for each phase sampling period. The phase signal may take any form from which it is possible to derive the time-lengths, or relative time-length, of sections of non-condensable gas over a phase sampling period.

It will be appreciated that references to a flow rate signal relating to the flow rate of the fluid flow indicates that a parameter substantially proportional to the flow rate of the fluid flow may be derived from the flow rate signal. Where the flow sensor is positioned downstream of a gas vent and generates the flow rate signal based on the condensate fraction of the fluid flow, the flow rate signal may substantially relate to the flow rate of the fluid flow as a whole by virtue that the non-condensable gas fraction accounts for a small fraction of the fluid flow.

We claim:

1. An apparatus for determining a non-condensable gas parameter relating to a total amount of non-condensable gas within a variable flow rate fluid flow containing both non-condensable gas and condensate, the apparatus comprising:
    a measurement tube configured to receive the fluid flow and arranged such that the fluid flow through the measurement tube comprises alternating sections of non-condensable gas and condensate;
    a flow sensor configured to generate a flow rate signal relating to the flow rate of the fluid flow in the measurement tube;
    a phase sensor configured to monitor over time the alternating sections of non-condensable gas and condensate flowing through the measurement tube and further arranged to generate a phase signal characteristic of the sections monitored; and
    a non-condensable gas determining unit configured to determine a non-condensable gas parameter relating to the total amount of non-condensable gas in the fluid flow based on the flow rate signal and the phase signal.

2. An apparatus according to claim 1, wherein the phase signal is a time-varying profile characteristic of the sections monitored.

3. An apparatus according to claim 2, wherein the determination of the non-condensable gas parameter comprises: correlating the phase signal with the flow rate signal.

4. An apparatus according to claim 1, wherein the determination of the a non-condensable gas parameter comprises correlating the phase signal with the flow rate signal.

5. An apparatus according to claim 1, wherein the determination of the a non-condensable gas parameter comprises determining the time-lengths of sections of at least one of non-condensable gas; and condensate from the phase signal, and correlating the at least one of the non-condensable gas and condensate with corresponding parts of the flow rate signal.

6. An apparatus according to claim 5, wherein the determination of the non-condensable gas parameter comprises calculating a non-condensable gas volume parameter proportional to the volume of the monitored sections of non-condensable gas.

7. An apparatus according to claim 6, further comprising:
    a temperature sensor configured to generate a temperature signal relating to the temperature of the fluid flow in the measurement tube, and wherein the non-condensable gas determining unit is configured to determine a non-condensable gas parameter relating to the total amount of non-condensable gas in the fluid flow at a baseline temperature different from the temperature of the fluid flow in the measurement tube based on the temperature signal, the flow signal and the phase signal.

8. An apparatus according to claim 1, further comprising:
    a temperature sensor configured to generate a temperature signal relating to the temperature of the fluid flow in the measurement tube, and wherein the non-condensable gas determining unit is configured to determine a non-condensable gas parameter relating to the total amount of non-condensable gas in the fluid flow at a baseline temperature different from the temperature of the fluid flow in the measurement tube based on the temperature signal, the flow signal and the phase signal.

9. An apparatus according to claim 8, wherein the phase sensor comprises an ultrasonic sensor configured to be responsive to the density of the fluid flow within the measurement tube.

10. An apparatus according to claim 1, wherein the non-condensable gas parameter represents the relative amount of non-condensable gas with respect to the amount of condensate or the amount of fluid flow.

11. An apparatus in accordance with claim 1 wherein the apparatus is in operative communication with a condenser of a steam installation that is arranged to receive a steam flow and configured to condense the steam flow to provide a fluid flow containing both non-condensable gas and condensate.

12. A method of determining a non-condensable gas parameter relating to a total amount of non-condensable gas within a variable flow rate fluid flow containing both non-condensable gas and condensate, the method comprising:
    receiving the fluid flow in a measurement tube to cause the fluid flow through a measurement tube to comprise alternating sections of non-condensable gas and condensate;
    generating a flow rate signal relating to the flow rate of the fluid flow in the measurement tube;
    monitoring the alternating sections of non-condensable gas and condensate flowing through the measurement tube over time;
    generating a phase signal characteristic of the sections monitored; and
        determining a non-condensable gas parameter relating to the total amount of non-condensable gas in the fluid flow based on the flow rate signal and the phase signal.

13. A method according to claim 12, wherein the phase signal is a time-varying profile characteristic of the sections monitored.

14. A method according to claim 12, wherein determining the non-condensable gas parameter comprises correlating the phase signal with the flow rate signal.

15. A method according to claim 12, wherein determining the non-condensable gas parameter comprises determining the time-lengths of sections of non-condensable gas and/or condensate from the phase signal, and correlating them with corresponding parts of the flow rate signal.

16. A method according to claim 15, wherein determining the non-condensable gas parameter comprises calculating a non-condensable gas volume parameter proportional to the volume of the monitored sections of non-condensable gas.

17. A method according to claim 16, further comprising:
generating a temperature signal relating to the temperature of the fluid flow in the measurement tube, and wherein the non-condensable gas parameter is determined to relate to the total amount of non-condensable gas in the fluid flow at a baseline temperature different from the temperature of the fluid flow in the measurement tube, based on the temperature signal, the flow signal and the phase signal.

18. A method according to claim 12, further comprising:
generating a temperature signal relating to the temperature of the fluid flow in the measurement tube, and wherein the non-condensable gas parameter is determined to relate to the total amount of non-condensable gas in the fluid flow at a baseline temperature different from the temperature of the fluid flow in the measurement tube, based on the temperature signal, the flow signal and the phase signal.

* * * * *